(12) United States Patent
Kim et al.

(10) Patent No.: US 11,900,599 B2
(45) Date of Patent: Feb. 13, 2024

(54) MULTI-MODALITY MEDICAL IMAGE ANALYSIS METHOD AND APPARATUS FOR BRAIN DISEASE DIAGNOSIS

(71) Applicant: PHENOMX INC., Seoul (KR)

(72) Inventors: Han Suk Kim, Suwon-si (KR); Young Sung Yu, Seoul (KR); Srinivasan Girish, Palatine, IL (US); Jae Woo Pi, Namyangju-si (KR); Thomas Nikita, Palatine, IL (US)

(73) Assignee: PHENOMX INC., Seoul (KR)

( * ) Notice: Subject to any disclaimer, the term of this patent is extended or adjusted under 35 U.S.C. 154(b) by 0 days.

(21) Appl. No.: 18/023,378

(22) PCT Filed: Dec. 3, 2021

(86) PCT No.: PCT/KR2021/018190
§ 371 (c)(1),
(2) Date: Feb. 26, 2023

(87) PCT Pub. No.: WO2023/095989
PCT Pub. Date: Jun. 1, 2023

(65) Prior Publication Data
US 2023/0334657 A1     Oct. 19, 2023

(30) Foreign Application Priority Data

Nov. 26, 2021  (KR) .......................... 10-2021-0165788

(51) Int. Cl.
*G06T 7/00* (2017.01)
*G16H 50/50* (2018.01)
(Continued)

(52) U.S. Cl.
CPC .......... *G06T 7/0012* (2013.01); *A61B 5/4842* (2013.01); *G16H 30/20* (2018.01);
(Continued)

(58) Field of Classification Search
CPC ......... G06T 7/0012; G06T 2207/10081; G06T 2207/10088; G06T 2207/10104;
(Continued)

(56) References Cited

U.S. PATENT DOCUMENTS 11,263,749 B1 * 3/2022 Purushottam .......... G16H 15/00

FOREIGN PATENT DOCUMENTS

KR   10-2015-0030974 A   3/2015
KR   10-2021-0056386 A   5/2021
KR   10-2021-0065768 A   6/2021

OTHER PUBLICATIONS

Heung-II NPL Hierarchical feature representation and multimodal fusion with deep learning for AD/MCI diagnosis (Year: 2014).*
(Continued)

*Primary Examiner* — Vu Le
*Assistant Examiner* — Winta Gebreslassie
(74) *Attorney, Agent, or Firm* — Bridgeway IP Law Group, PLLC; Sang Ho Lee; Hyun Woo Shin (57) ABSTRACT

Provided is a multi-modality medical image analysis method and apparatus for brain disease diagnosis. The method includes the steps of: acquiring medical images with different modalities for the same patient; selecting at least some of pre-trained analysis models corresponding to the modalities of the medical images; inputting the medical images correspondingly to the analysis models selected with respect to the modalities of the medical image to produce output values related to a plurality of factors used for reading at least one brain disease; converting the output values to produce a plurality of feature vectors corresponding to the output values; and inputting the plurality of feature vectors to at least one diagnosis model pre-trained to read the brain disease to thus predict a degree of brain disease progression.

10 Claims, 4 Drawing Sheets

(51) Int. Cl.
*G16H 30/20* (2018.01)
*G16H 50/70* (2018.01)
*A61B 5/00* (2006.01)

(52) U.S. Cl.
CPC ............. *G16H 50/50* (2018.01); *G16H 50/70* (2018.01); *G06T 2207/10081* (2013.01); *G06T 2207/10088* (2013.01); *G06T 2207/10104* (2013.01); *G06T 2207/20081* (2013.01); *G06T 2207/30016* (2013.01); *G06T 2207/30096* (2013.01); *G06T 2207/30101* (2013.01)

(58) Field of Classification Search
CPC . G06T 2207/20081; G06T 2207/30016; G06T 2207/30096; G06T 2207/30101; G16H 50/50; G16H 30/20; G16H 50/70; A61B 5/4842
See application file for complete search history.

(56) References Cited

OTHER PUBLICATIONS

Zhou, Tao et al., "Effective feature learning and fusion of multimodality data using stage-wise deep neural network for dementia diagnosis", Human Brain Mapping, Nov. 1, 2018, pp. 1001-1016.
Venugopalan, Janani et al., "Multimodal deep learning models for early detection of Alzheimer's disease stage", Scientific Reports, Feb. 5, 2021, pp. 1-13.
Carnevale, Lorenzo et al., "Innovative MRI techniques in neuroimaging approaches for cerebrovascular diseases and vascular cognitive impairment", International Journal of Molecular Sciences, May 30, 2019, pp. 1-15.
Kroll, Hannes et al., "Resting state Bold Mri for perfusion and ischemia", Topics in Magnetic Resonance Imaging, Apr. 2017, pp. 91-96.

* cited by examiner

MULTI-MODALITY MEDICAL IMAGE ANALYSIS METHOD AND APPARATUS FOR BRAIN DISEASE DIAGNOSIS

TECHNICAL FIELD

The present disclosure relates to a multi-modality medical image analysis method and apparatus for brain disease diagnosis.

BACKGROUND ART

Generally, a plurality of imaging modalities is obtained from a single patient. Current imaging analysis is performed by recording a radiology doctor's comment on medical images, making a final diagnosis for a patient's disease or determining his or her treatment process by his or her specialist, based on the recorded comment, and providing appropriate treatment and prescription for the patient.

In analyzing a plurality of images or recordings to determine a treatment adequate for the patient, a lot of time and efforts of the specialist are needed so as to totally diagnose the patient's disease based on the analysis results for the plurality of images, and further, a lot of knowledge and experiences of the specialist are needed so as to perform mutual understanding with the patient and determine a treatment method of the patient. To obtain such things, a lot of time, training, and trial and error are required, which results in high costs. In determining the patient's disease, besides, the specialist's prejudice may be involved, thereby causing a misdiagnosis, and otherwise, there is a high probability that some of comorbidities occurring at the same time may be lost.

Further, a method for structurally analyzing brain regions automatically from a computed tomography (CT) image or magnetic resonance imaging (MRI) image using an artificial intelligence technology has been at present utilized in real clinical trials. As a representative technology, an anatomically or pathologically meaningful region is segmented, and next, changes in size and shape of the corresponding region are analyzed from a plurality of region-related medical images for a given period of time. However, the diagnosis obtained through such structural analysis is made when a patient's disease is already progressed to a given degree, and if the patient is normal or has a mild disease, there is a limitation that it is hard to distinguish a difference between images caused by his or her disease and a difference caused by his or her growth and genetic factors.

Further, functional Magnetic Resonance Imaging (fMRI) has been clinically performed to detect a blood-oxygen-level dependent (BOLD) signal that is activated during a patient's resting state, build a network connecting detailed regions of the brain, and analyze the network. However, the activated region of the brain has a lot of noise, and there is a limitation that signal differences by function and organ of the brain are not accurately identified. That is, there is a high probability that the analyzed BOLD data is false positive, and accordingly, diagnosing a disease only with the fMRI is avoided, which is a current trend.

Positron Emission Tomography (PET) is a technique that senses a body's biochemical changes and thus performs imaging for the changes. Generally, an extreme amount of radioactive material is injected into the body, and if the radioactive material is actively dissolved, it appears as high pixel values on high quality images. However, types of radioactive materials may be different according to types of diseases to be diagnosed, and accordingly, PET images may have a plurality of specific modalities.

Therefore, there is a need for a new analysis method for diagnosing a disease rapidly and accurately using multiple types of medical images.

DISCLOSURE

Technical Problem

Accordingly, it is an object of the present disclosure to provide a multi-modality medical image analysis method and apparatus for brain disease diagnosis that is capable of analyzing multi-modality medical images through a plurality of analysis models and thus producing a plurality of diagnosis models according to brain diseases to be diagnosed, thereby drastically reducing the time required for the diagnosis and enhancing diagnosis accuracy.

The technical problems of the multi-modality medical image analysis method and apparatus to be achieved through the present disclosure are not limited as mentioned above, and other technical problems not mentioned herein will be obviously understood by one of ordinary skill in the art through the following description.

Technical Solution

To accomplish the above-mentioned objects, according to an aspect of the present disclosure, there is provided a multi-modality medical image analysis method for brain disease diagnosis, the method including the steps of: acquiring medical images with different modalities for the same patient; selecting at least some of pre-trained analysis models corresponding to the modalities of the medical images; inputting the medical images correspondingly to the analysis models selected with respect to the modalities of the medical image to produce output values related to a plurality of factors used for reading at least one brain disease; converting the output values to produce a plurality of feature vectors corresponding to the output values; and inputting the plurality of feature vectors to at least one diagnosis model pre-trained to read the brain disease to thus predict a degree of brain disease progression.

According to an exemplary embodiment of the present disclosure, the method may further include the step of training the respective analysis models so as to output the output values related to the plurality of factors, based on the medical images with the different modalities.

According to an exemplary embodiment of the present disclosure, the medical images may include at least two or more images selected from Magnetic Resonance Imaging (MRI) images, Computed Tomography images for brain angiography, functional Magnetic Resonance Imaging (fMRI) images, and Positron Emission Tomography-Computed Tomography (PET-CT) images, for the patient's brain.

According to an exemplary embodiment of the present disclosure, if the medical images are the MRI images, the output values may be values corresponding to at least one of the percentages of a plurality of brain regions and the fat amounts of the head and neck.

According to an exemplary embodiment of the present disclosure, if the medical images are the CT images for brain angiography, the output values may be values corresponding to existence/non-existence of abnormal blood vessels in the plurality of brain regions.

According to an exemplary embodiment of the present disclosure, if the medical images are the fMRI images, the output values may be values corresponding to the relations among the plurality of brain regions activated or non-activated simultaneously in a state where the patient takes rest.

According to an exemplary embodiment of the present disclosure, if the medical images are the PET-CT images, the output values may be values corresponding to a degree of severity of at least one of a tumor, dementia, a Parkinson's disease, and epilepsy.

According to an exemplary embodiment of the present disclosure, the step of producing a plurality of feature vectors may include the step of standardizing or normalizing the output values by means of feature scaling.

According to an exemplary embodiment of the present disclosure, the method may further include the step of detecting, if there is a defect analysis model of the analysis model that does not have the medical images with the modalities corresponding thereto, medical images of another patient having the same disease, the step of producing output values related to a plurality of factors including the step of performing imputation of the defect analysis model with the detected medical images of another patient to output the output values.

To accomplish the above-mentioned objects, according to another aspect of the present disclosure, there is provided a multi-modality medical image analysis apparatus for brain disease diagnosis, the apparatus including: at least one processor; and a memory for storing a program executable by the processor, wherein the processor executes the program to acquire medical images with different modalities for the same patient, select at least some of pre-trained analysis models corresponding to the modalities of the medical images, input the medical images correspondingly to the analysis models selected with respect to the modalities of the medical image to produce output values related to a plurality of factors used for reading at least one brain disease, convert the output values to produce a plurality of feature vectors corresponding to the output values, input the plurality of feature vectors to at least one diagnosis model pre-trained to read the brain disease, and predict a degree of brain disease progression.

Advantageous Effects of the Invention

According to the embodiments of the present disclosure, the multi-modality medical image analysis method and apparatus can analyze the multi-modality medical images through the plurality of analysis models and thus produce the plurality of diagnosis models according to the brain diseases to be diagnosed, thereby drastically reducing the time required for the diagnosis and enhancing diagnosis accuracy.

The effectiveness of the multi-modality medical image analysis method and apparatus according to the present disclosure is not limited as mentioned above, and it should be understood to those skilled in the art that the effectiveness of the disclosure may include another effectiveness as not mentioned above from the detailed description of the present disclosure.

BRIEF DESCRIPTION OF DRAWINGS

Now, a brief description of the drawings is given to allow the drawings suggested in the present disclosure to be more clearly understood.

MODE FOR DISCLOSURE

The present disclosure may be modified in various ways and may have several exemplary embodiments. Specific exemplary embodiments of the present disclosure are illustrated in the drawings and described in detail in the detailed description. However, this does not limit the disclosure within specific embodiments and it should be understood that the disclosure covers all the modifications, equivalents, and replacements within the idea and technical scope of the disclosure.

In the description, if it is determined that the detailed explanation on the well known technology related to the present disclosure makes the scope of the present disclosure not clear, the explanation will be avoided for the brevity of the description. Terms, such as the first, the second, and the like may be used to describe various elements, but the elements should not be restricted by the terms. The terms are used to only distinguish one element from the other element.

When it is said that one element is described as being "connected" or "coupled" to the other element, one element may be directly connected or coupled to the other element, but it should be understood that another element may be present between the two elements.

The terms "unit", "-or/er" and "module" described in the specification indicate a unit for processing at least one function or operation, which may be implemented by hardware, software or a combination thereof, such as a processor, a micro processor, a micro controller, a central processing unit (CPU), a graphics processing unit (GPU), an accelerate processor unit (APU), a digital signal processor (DSP), an application specific integrated circuit (ASIC), a field programmable gate array (FPGA), and the like.

Further, it should be appreciated that the division of the parts in the present disclosure is just made according to principal functions the parts have. That is, two or more parts as will be discussed below may be combined to one part or one part may be divided into two or more parts according to more specified functions. Moreover, the respective parts as will be discussed in the specification can additionally perform some or all of functions performed by other parts as well as their main functions, and of course, also, some of the main functions of the respective parts can be performed only by other parts.

A method according to an embodiment of the present invention may be performed in a personal computer, a work station, a server computer, and the like, which have operation ability, or in a separate device therefor.

Further, the method may be performed in one or more operation devices. For example, at least one or more steps of a method 100 according to an embodiment of the present disclosure are performed in a client device, and other steps in a server device. In this case, the client device and the server device are connected to each other by a network and transmit and receive the results of operations to and from each other. Otherwise, the method 100 according to the present disclosure may be performed through distributed computing.

Hereinafter, embodiments of the present disclosure will be described in detail sequentially.

Figure 1:
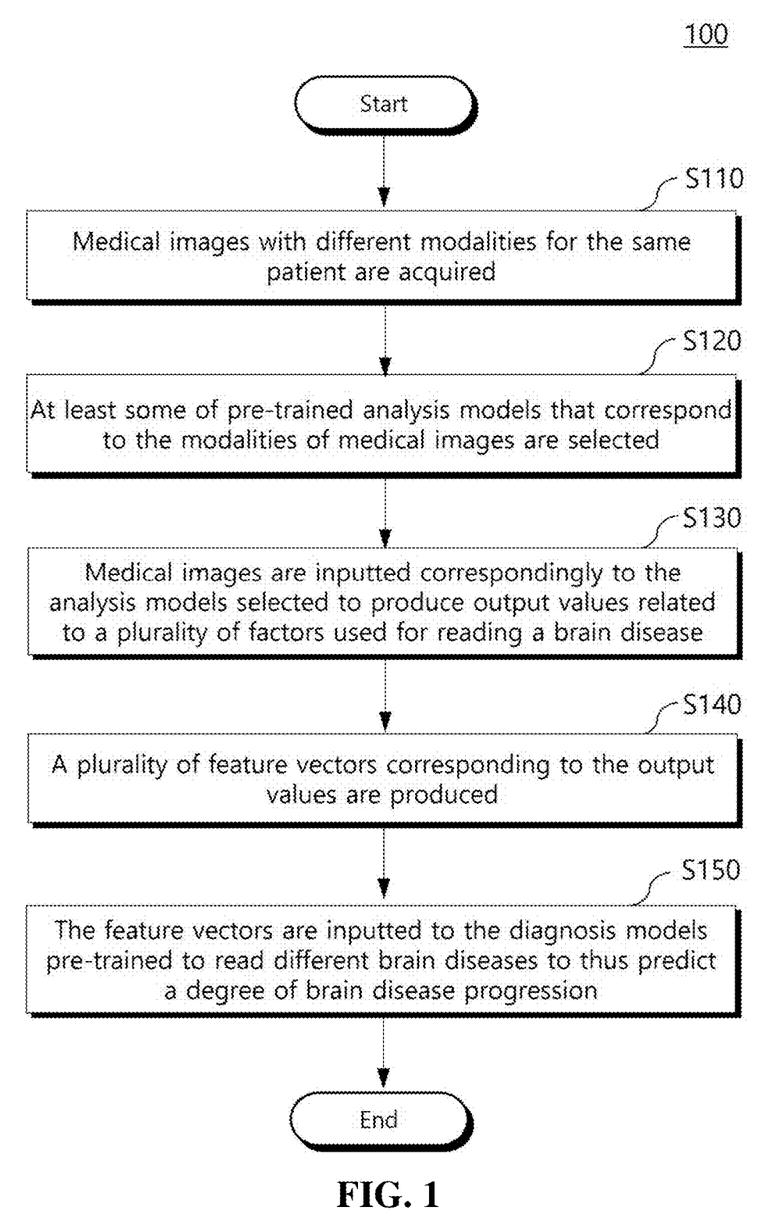
FIG. 1 is a flowchart showing a multi-modality medical image analysis method for brain disease diagnosis according to an embodiment of the present disclosure.

FIG. 1 is a flowchart showing a multi-modality medical image analysis method for brain disease diagnosis according to an embodiment of the present disclosure.

At step S110, a plurality of medical images having different modalities, that is, different types of medical images for the same patient kinds are acquired from an apparatus.

For example, the medical images are received from an external database server or acquired from an imaging device connected to the apparatus by means of wired and wireless communication.

In the embodiment of the present disclosure, the medical images may include at least two or more images selected from a Magnetic Resonance Imaging (MRI) image, a Computed Tomography image for brain angiography, a functional Magnetic Resonance Imaging (fMRI) image, and a Positron Emission Tomography-Computed Tomography (PET-CT) image, which are produced by imaging a body region (for example, the head and neck) including the brain using given methods or imaging devices.

According to the embodiment of the present disclosure, further, the PET-CT medical image may have a plurality of different modalities according to types of contrast agents and imaging methods. For example, the PET-CT medical image may include an image with different modalities, such as F-18 FDGBrain PET/CT, F-18 FDOPA Brain PET/CT, F-18 FP-CIT Brain PET/CT, F-18 Florbetaben Brain PET/CT, C-11 Methionine Brain PET/CT, C-11 PIB Brain PET/CT, and the like.

At step S120, at least some of a plurality of pre-trained analysis models that correspond to the respective modalities of the medical images are selected as application models by the apparatus.

In this case, each analysis model is pre-trained to analyze the medical image with a specific modality, and the analysis models adequate for the medical images are selected from the plurality of analysis models according to the modalities of the medical images acquired at the step S110.

To do this, each analysis model includes at least one network function. That is, the network function is pre-trained to output given data from each modality medical image through training data.

In this case, the network function may be used with the same meaning as a neural network. In this case, the neural network is composed of interconnected calculation units, which are commonly called nodes, and the nodes are called neurons. Generally, the neural network is made up of a plurality of nodes. The nodes for constituting the neural network are connected to one another by means of one or more links. In this case, some of nodes constituting the neural network build one layer based on their distances from an initial input node. For example, a collection of nodes with the distances of n from the initial input node builds an n layer. The neural network may include a deep neural network (DNN) having a plurality of hidden layers as well as input and output layers.

In the embodiment of the present disclosure, the analysis models may include at least one structural analysis model, at least one functional analysis model, and at least one biochemical analysis model. For example, the structural analysis model segments specific brain regions from a brain MRI image and thus outputs proportions of the segmented regions or segments fat regions from the brain and thus outputs the percentage of fat. Further, the structural analysis model extracts blood vessels from a brain angiography CT image and thus outputs existence/non-existence of abnormal blood vessels by detailed region of the brain. Further, for example, the functional analysis model extracts active and/or non-active regions of the brain from an fMRI image and thus outputs relations between the active and/or non-active regions. Moreover, for example, the biochemical analysis model produces evaluation values for severity of a disease from a PET-CT image.

At step S130, the medical images are inputted correspondingly to the analysis models selected with respect to the modalities of the medical images to produce output values related to a plurality of factors used for reading at least one brain disease.

In the embodiment of the present disclosure, if the medical images are the MRI images, the output values of the analysis model are values corresponding to at least one of the percentages of brain regions and the fat amounts of the head and neck. For example, the analysis model segments a patient's brain into a plurality of brain regions based on an anatomical structure of the brain and thus outputs, as the output values, the percentages of the brain regions segmented in the entire brain region. Further, for example, the analysis model segments fat regions from the brain MRI image and thus outputs, as the output values, the percentages occupied by the fat regions in the entire brain region.

In the embodiment of the present disclosure, if the medical images are the brain angiography CT images, the output values of the analysis model are values corresponding to existence/non-existence of abnormal blood vessels in a plurality of brain regions. For example, the output values include positions, volumes, and shapes of abnormal blood vessels, cerebral aneurysm existence/non-existence, arteriosclerosis existence/non-existence, and the like.

In the embodiment of the present disclosure, if the medical images are the fMRI images, the output values of the analysis model are values corresponding to the relations among a plurality of brain regions activated or non-activated simultaneously in a state where a patient takes rest. For example, the analysis model outputs, as the output values, networks connecting the activated brain regions in the form of an adjacency matrix. In this case, the higher each row and column value is, the higher a degree of connectivity is.

In the embodiment of the present disclosure, if the medical images are the PET-CT images, the output values of the analysis model are values corresponding to a degree of severity of at least one of a tumor, dementia, a Parkinson's disease, and epilepsy. For example, the analysis model is differently obtained according to the modalities of the PET-CT and thus outputs the evaluation values for the degree of severity of the brain disease from the PET-CT images with different modalities.

In the embodiment of the present disclosure, the method 100 may further include the step of training the respective analysis models so as to output the output values. In this case, each analysis model is trained to thus output the output values, based on the medical images with the different modalities. For example, the structural analysis model is trained with the medical images including a plurality of MRI images or a plurality of brain angiography CT images, as training data, and the functional analysis model is trained with the medical images including a plurality of MRI images, as training data. Further, for example, the biochemical analysis model is trained with the medical images including a plurality of PET-CT images with the same modality, as training data.

In the embodiment of the present disclosure, the method 100 may further include the steps of detecting medical images of another patient having the same disease with a defect analysis model of the analysis model where the medical images with the corresponding modalities do not exist and replacing the input values of the defect analysis model by another patient's medical images. This means a kind of data augmentation, and through the step, a degree of accuracy in prediction of the analysis model is more improved.

At step S140, the output values of the analysis models are converted in a given method to produce a plurality of feature vectors corresponding thereto.

In the embodiment of the present disclosure, the step S140 is carried out by means of vector encoding.

In the embodiment of the present disclosure, the step S140 further includes the step of standardizing or normalizing the output values by means of feature scaling. That is, if the ranges or numerical values of the respective output values are different or if specific output values are too high or low, errors in the data training may occur, and further, the standardization or normalization for the feature vectors is performed in training diagnosis models as will be discussed below. At the step S140, the output values of the analysis models at the step S130 can be converted to the same scales with applied upon the training of the diagnosis models.

For example, the standardization represents a method for converting a normal distribution into a standard normal distribution with a mean of zero and a standard deviation of 1, and the normalization represents a method for converting the output values into values between 0 and 1.

At step S150, the plurality of feature vectors are inputted to the diagnosis models to predict a degree of brain disease progression. In this case, one or more diagnosis models are provided correspondingly to different brain diseases.

In the embodiment of the present disclosure, the diagnosis models are trained to convert the output values from the analysis models in the step of training the analysis models into the feature vectors and thus predict the degree of brain disease progression with the converted feature vectors as the training data. To do this, each diagnosis model has at least one network function.

For example, the diagnosis models predict the degree of progression for brain diseases such as dementia, a Parkinson's disease, a malignant brain tumor, and or epilepsy.

In the embodiment of the present disclosure, the method 100 further includes the steps of receiving a user's input for selecting the brain disease to be diagnosed and selecting the diagnosis model to be applied, based on the user's input.

FIGS. 2A to 2d are exemplary diagrams showing the analysis models for performing multi-modality medical image analysis according to the embodiment of the present disclosure.

As shown, the number of analysis models corresponds to the number of modalities of the medical images, and for example, the analysis models include at least one structural analysis model, at least one functional analysis model, and/or at least one biochemical analysis model.

Figure 2A:
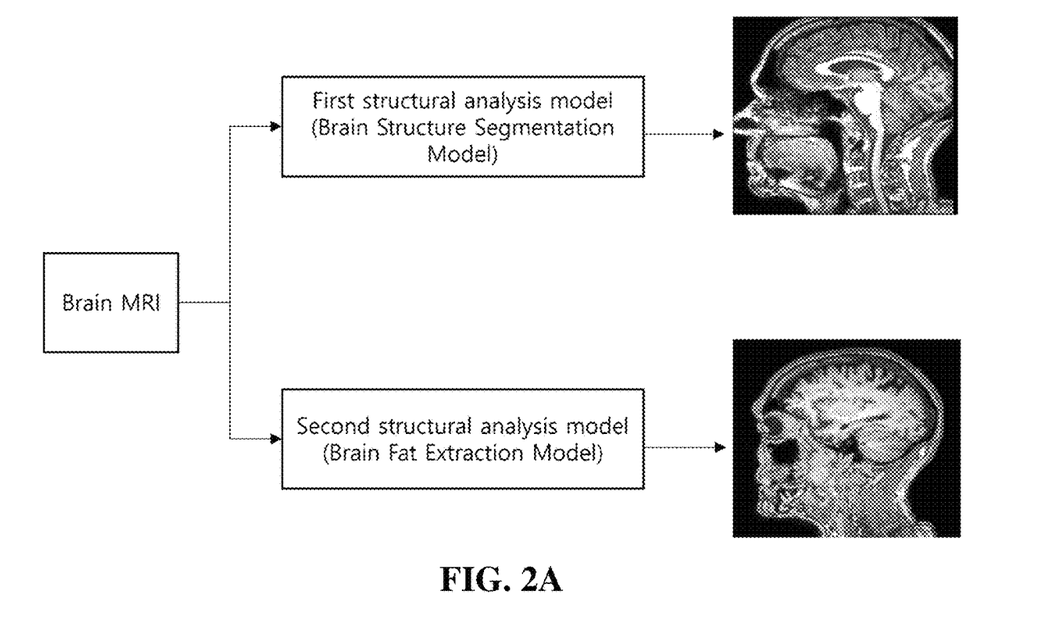
FIGS. 2A to 2D are exemplary diagrams showing analysis models for performing multi-modality medical image analysis according to the embodiment of the present disclosure.

Referring to FIG. 2A, if the medical images are the MRI images for the patient's head and neck including the brain, a first structural analysis model and a second structural analysis model are selected as application models, and next, the MRI images are inputted to the analysis models.

The first structural analysis model segments a plurality of brain regions and the entire brain region including the plurality of brain regions from the MRI image through the trained network function and thus outputs the percentages of the brain regions occupied in the entire brain region.

Further, the second structural analysis model extracts fat regions from the MRI image and thus outputs the percentages of the fat regions occupied in the entire brain region or head and neck.

Figure 2B:
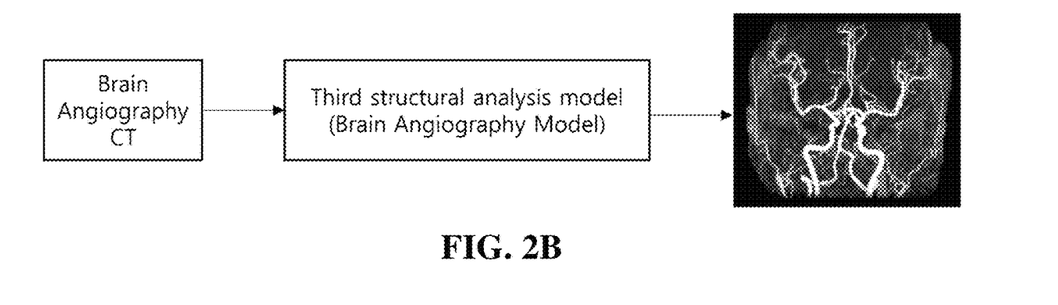

Referring to FIG. 2B, if the medical images are the brain angiography CT images, a third structural analysis model is selected as an application model, and accordingly, the third structural analysis model segments a plurality of brain regions or blood vessel regions and thus outputs evaluation values for the positions, volumes, and shapes of abnormal blood vessels, cerebral aneurysm existence/non-existence, arteriosclerosis existence/non-existence, and the like.

Figure 2C:
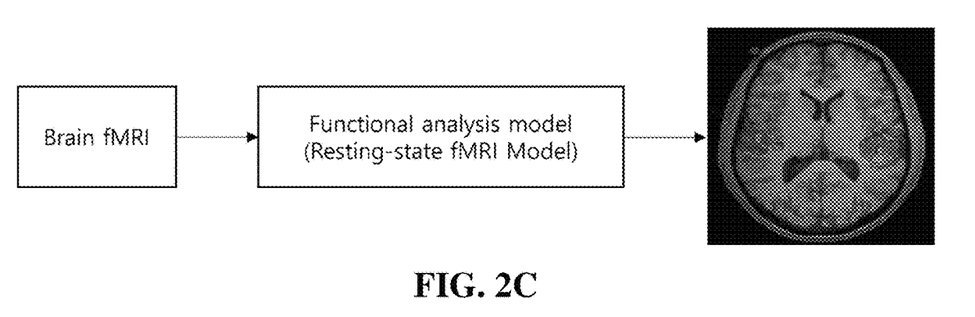

Referring to FIG. 2C, if the medical images are the fMRI images, a functional analysis model is selected as an application model, and accordingly, the functional analysis model extracts brain regions activated or non-activated simultaneously in a state where the patient takes rest and thus outputs the adjacency matrix representing the connection relations among the extracted brain regions.

Figure 2D:
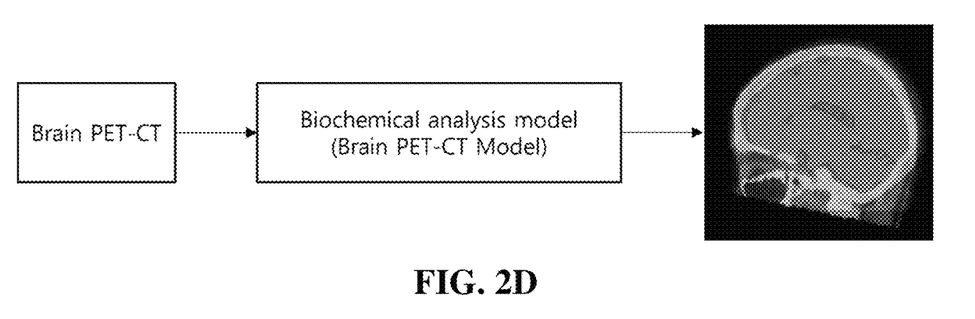

Referring to FIG. 2D, if the medical images are the PET-CT images, a biochemical analysis model is selected as an application model, and accordingly, the biochemical analysis model outputs evaluation values for a degree of severity of a brain disease such as a tumor, dementia, a Parkinson's disease, and epilepsy.

Figure 3:
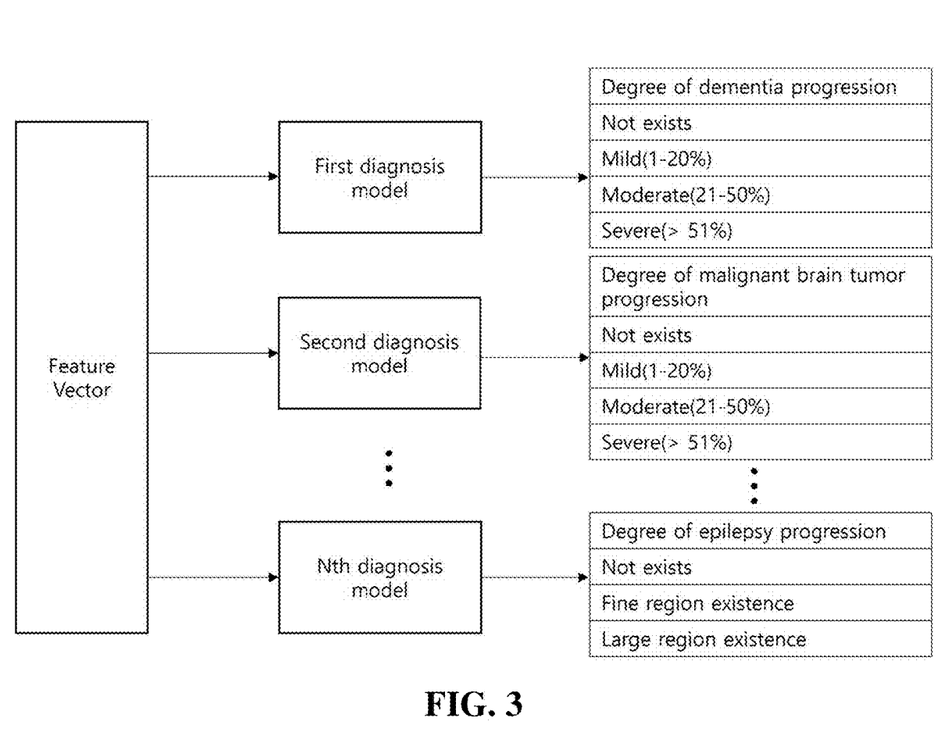
FIG. 3 is an exemplary block diagram showing diagnosis models for predicting brain diseases using feature vectors corresponding to the output values from the analysis models according to the embodiment of the present disclosure.

FIG. 3 is an exemplary block diagram showing the diagnosis models for predicting brain diseases using the feature vectors corresponding to the output values from the analysis models according to the embodiment of the present disclosure.

As shown, the number of diagnosis models is determined correspondingly to one or more brain diseases. If the user's input for selecting the brain disease to be diagnosed is performed, the diagnosis model corresponding to the user's input is selected from the plurality of diagnosis models, and the feature vectors produced by converting the output values of the plurality of analysis models are inputted to the selected diagnosis model.

The network function included in the diagnosis model outputs prediction values for the degree of progression for the brain disease selected by the user, based on the inputted feature vectors.

In the embodiment of the present disclosure, if the brain disease selected by the user is dementia, the diagnosis model reads detailed types of dementia (Alzheimer's disease, alcohol related dementia, vascular dementia, dementia with Lewy bodies, frontotemporal dementia, etc.) and thus predicts a degree of dementia progression, based on the feature vectors.

Figure 4:
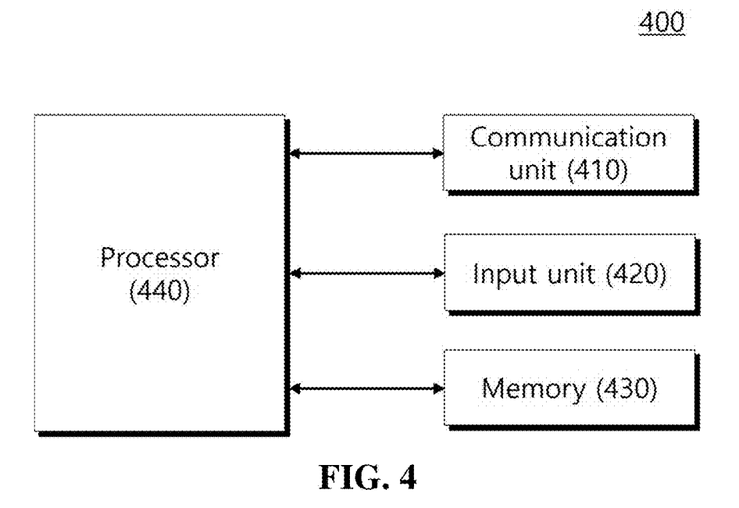
FIG. 4 is a schematic block diagram showing a multi-modality medical image analysis apparatus for brain disease diagnosis according to another embodiment of the present disclosure.

FIG. 4 is a schematic block diagram showing a multi-modality medical image analysis apparatus 400 according to another embodiment of the present disclosure.

A communication unit 410 receives input data (medical images, etc.) for analyzing the medical images. The communication unit 410 includes wired and wireless communication units. If the communication unit 410 includes the wired communication unit, the communication unit 410 includes one or more components for performing communication with a local region network (LAN), a wide region network (WAN), a value added network (VAN), a mobile radio communication network, a satellite communication network, and a combination thereof. Further, if the communication unit 410 includes the wireless communication unit, the communication unit 410 transmits and receives data or signals wirelessly by using cellular communication, wireless LAN (e.g., Wi-Fi), and the like. According to the present disclosure, the communication unit 410 transmits and receives data or signals to and from an external device or external server under the control of a processor 440 as will be discussed later.

An input unit 420 receives various user commands through external control. To do this, the input unit 420 includes one or more input devices or is connected to the input devices. For example, the input unit 420 is connected to an interface for various inputs such as a keypad, a mouse, and the like and receives the user commands from the interface. To do this, the input unit 420 includes an interface such as a USB port, a Thunderbolt interface, and the like. Further, the input unit 420 includes various input devices such as a touch screen, a button, and the like or is connected to the input devices to receive the user commands from the outside.

A memory 430 stores programs and/or program commands for operating the processor 440 and temporarily or permanently stores data inputted and outputted. The memory 430 includes at least one storage medium of a flash memory, a hard disc, a multimedia card micro storage medium, a card type memory (e.g., SD or XD memory), random access memory (RAM), a static RAM (SRAM), a read-only memory (ROM), an electrically erasable programmable ROM (EEPROM), a programmable ROM (PROM), a magnetic memory, a magnetic disc, and an optical disc.

Further, the memory 430 stores various network functions and algorithms, while storing various data, programs (with one or more instructions), applications, software, commands, and codes for operating and controlling an apparatus 400 according to the present disclosure.

The processor 440 controls all of operations of the apparatus 400. The processor 440 executes one or more programs stored in the memory 430. The processor 440 represents a central processing unit (CPU), a graphics processing unit (GPU), or a dedicated processor through which the method according to the technical ideas of the present disclosure is performed.

According to the embodiment of the present disclosure, the processor 440 acquires medical images with different modalities for the same patient, selects at least some of pre-trained analysis models corresponding to the modalities of the medical images, inputs the medical images correspondingly to the analysis models selected with respect to the modalities of the medical image to produce output values related to a plurality of factors used for reading at least one brain disease, converts the output values to produce a plurality of feature vectors corresponding to the output values, and inputs the plurality of feature vectors to at least one diagnosis model pre-trained to read the brain disease to thus predict a degree of brain disease progression.

According to the embodiment of the present disclosure, the processor 440 trains the respective analysis models so as to output the output values related to the plurality of factors, based on the medical images with the different modalities.

According to the embodiment of the present disclosure, the processor 440 standardizes or normalizes the output values by means of feature scaling.

According to the embodiment of the present disclosure, the processor 440 detects, if there is a defect analysis model of the analysis model that does not have the medical images with the modalities corresponding thereto, medical images of another patient having the same disease and performs imputation of the defect analysis model with the detected medical images of another patient to output the output values.

The various embodiments of the present disclosure as described above may be implemented in the form of a program instruction that can be performed through various computers, and may be recorded in a computer readable recording medium. The computer readable medium may include a program command, a data file, a data structure, and the like independently or in combination. The program instruction recorded in the recording medium is specially designed and constructed for the present disclosure, but may be well known to and may be used by those skilled in the art of computer software. The computer readable recording medium may include a magnetic medium such as a hard disc, a floppy disc, and a magnetic tape, an optical recording medium such as a compact disc read only memory (CD-ROM) and a digital versatile disc (DVD), a magneto-optical medium such as a floptical disk, and a hardware device specifically configured to store and execute program instructions, such as a read only memory (ROM), a random access memory (RAM), and a flash memory. Further, the program command may include a machine language code generated by a compiler and a high-level language code executable by a computer through an interpreter and the like.

Further, the method according to the disclosed embodiments of the present disclosure is included in a computer program product. The computer program product as a product may be traded between a seller and a buyer.

The computer program product may include an S/W program and a computer readable storage medium in which the S/W program is stored. For example, the computer program product may include an S/W program type product (e.g., downloadable app) electronically distributed through a manufacturing company of an electronic device or electronic market (e.g., Google play store, an app store, etc.). To do such electronic distribution, at least a portion of the S/W program may be stored in the storage medium or temporarily produced. In this case, the storage medium may be a storage medium of a server of the manufacturing company, a server of the electronic market, or a broadcast server for temporarily storing the S/W program.

The computer program product may include a storage medium of a server or a storage medium of a client device in a system composed of the server and the client device. If a third device (e.g., smartphone) connected to the server or client device exists, the computer program product may include a storage medium of the third device. Otherwise, the computer program product may include an S/W program itself transmitted from the server to the client device or the third device or from the third device to the client device.

In this case, one of the client device and the third device executes the computer program product to perform the method according to the embodiments of the present disclosure. Further, two or more devices of the server, the client device and the third device execute the computer program product to distributedly perform the method according to the embodiments of the present disclosure.

For example, the server (e.g., a cloud server or artificial intelligence server) executes the computer program product stored therein and controls the client device connected thereto to perform the method according to the embodiments of the present disclosure.

While the present disclosure has been described with reference to the particular illustrative embodiments, it is not to be restricted by the embodiments but only by the appended claims. It is to be appreciated that those skilled in the art can change or modify the embodiments without departing from the scope and spirit of the present disclosure.

The invention claimed is:

1. A multi-modality medical image analysis method for brain disease diagnosis, which is executed by a medical image analysis apparatus having at least one processor, the method comprising:
   acquiring medical images with different modalities for a patient;
   selecting, from a plurality of pre-trained analysis models, the analysis models having modalities corresponding to the modalities of the acquired medical images;
   inputting the medical images correspondingly to the analysis models selected with respect to the modalities of the medical images to produce output values related to a plurality of factors related to at least one brain disease;
   converting the output values to produce a plurality of feature vectors corresponding to the output values; and
   inputting the plurality of feature vectors to at least one or more diagnosis models pre-trained to predict a degree of progression of the at least one brain disease,
   wherein when there is a defect analysis model of the analysis models that does not have the medical images with the modalities corresponding thereto, the method further comprises detecting medical images of another patient having the same brain disease, and
   wherein the producing the output values related to the plurality of factors comprises performing imputation of the defect analysis model with the detected medical images of the another patient to output the output values.

2. The method according to claim 1, further comprising training the respective analysis models so as to output the output values related to the plurality of factors, based on the medical images with the different modalities.

3. The method according to claim 1, wherein the medical images comprise at least two or more images selected from Magnetic Resonance Imaging (MRI) images, Computed Tomography images for brain angiography, functional Magnetic Resonance Imaging (fMRI) images, and Positron Emission Tomography-Computed Tomography (PET-CT) images, for the patient's brain.

4. The method according to claim 3, wherein when the medical images are the MRI images, the output values are values corresponding to at least one of percentages of a plurality of brain regions and fat amounts of a head and a neck of the patient.

5. The method according to claim 3, wherein when the medical images are the brain angiography CT images, the output values are values corresponding to existence/non-existence of abnormal blood vessels in a plurality of brain regions.

6. The method according to claim 3, wherein when the medical images are the fMRI images, the output values are values corresponding to a plurality of brain regions activated or non-activated simultaneously in a state where the patient takes rest.

7. The method according to claim 3, wherein when the medical images are the PET-CT images, the output values are values corresponding to a degree of severity of at least one of a tumor, dementia, a Parkinson's disease, and epilepsy.

8. The method according to claim 1, wherein the producing the plurality of feature vectors comprises standardizing or normalizing the output values by means of feature scaling.

9. A multi-modality medical image analysis apparatus for brain disease diagnosis, the apparatus comprising:
   at least one processor; and
   a memory for storing a program executable by the processor,
   wherein the at least one processor is configured to execute the program to:
   acquire medical images with different modalities for a patient;
   select, from a plurality of pre-trained analysis models, the analysis models having modalities corresponding to the modalities of the acquired medical images;
   input the medical images correspondingly to the analysis models selected with respect to the modalities of the medical images to produce output values related to a plurality of factors related to at least one brain disease;
   convert the output values to produce a plurality of feature vectors corresponding to the output values;
   input the plurality of feature vectors to at least one or more diagnosis models pre-trained to predict a degree of progression of the at least one brain disease; and
   and when there is a defect analysis model of the analysis models that does not have the medical images with the modalities corresponding thereto, medical images of another patient having the same brain disease are detected to perform imputation of the defect analysis model with the detected medical images of the another patient with respect to the defect analysis model and output the output values.

10. A computer program stored in a non-transitory recording medium to execute the method according to claim 1.

* * * * *